United States Patent [19]
Kethley

[11] 4,409,834
[45] Oct. 18, 1983

[54] EVAPOPSYCHROMETER

[76] Inventor: Lancelot I. Kethley, 840 York St., #8, Oakland, Calif. 94610

[21] Appl. No.: 273,339

[22] Filed: Jun. 15, 1981

[51] Int. Cl.³ .............................................. G01N 1/04
[52] U.S. Cl. ...................................... 73/336; 73/338; 374/39
[58] Field of Search ..................... 73/338, 76, 77, 336, 73/335, 193 A, 193 R, 338.6

[56] References Cited

U.S. PATENT DOCUMENTS

Re. 12,727  12/1907  Cramer ................................ 73/338
 1,670,507   5/1928  Jose ..................................... 73/338

FOREIGN PATENT DOCUMENTS 350151  10/1905  France ................................. 73/338
296110   5/1932  Italy ................................... 73/338
217531  10/1941  Switzerland ..................... 73/193 A
  1341  of 1912  United Kingdom .................. 73/338

*Primary Examiner*—Charles A. Ruehl
*Assistant Examiner*—Denis E. Corr

[57] ABSTRACT

The evapopsychrometer is a special combination of an evaporimeter and a psychrometer. This combination was made possible by the application of a feeder in between and by the use of that portion of the wick which covers the bulb of one of the thermometers as the evaporating surface.

4 Claims, 4 Drawing Figures

EVAPOPSYCHROMETER

BACKGROUND OF THE INVENTION

There are several devices available claiming to determine the rate of evaporation, such as the Piche evaporimeter, clay atmometer, pan evaporimeter and a wide variety of lysimeters. While all of these devices yield data for the evaporated amount of water in a selected period of time, it is understood that those obtained data are only representative of the devices from which the data were obtained. The main problem is that the common standard for the determination of the state of the air, the psychrometer, is separated from the above listed devices while all of them acquire their own temperatures.

There are also psychrometers with reservoirs, but they do not function as evaporimeters. On the one hand, the reservoirs are not made to register a change in the water supply. On the other hand, the reservoirs are substantially open around the wick and the wet bulb. Because of this, evaporation takes place not just from the web bulb, but also from the entire wick and from the water in the reservoir. This evaporation affects the condition of the air in the close vicinity of the wet bulb and hinders the evaporation from it. This results in the incorrect evaluation of the conditions of the surrounding air. None of these psychrometers allows the evaporation to be related to the well defined surface of that portion of the wick which covers the wet bulb. For the above reasons the rate of evaporation from the unit surface cannot be determined by the use of these psychrometers.

The equations, mainly the different modifications of the Penman equation, are derived to calculate the rate of evaporation by the use of psychrometric and wind data with the assumption that to a certain extent the psychrometric data near the ground already reflect the condition of the ground, including the vegetation on it, as well as the absorptive ability of the air. The calculated results, however, are expected to be checked against some sort of observational data of actual evaporation.

SUMMARY OF THE INVENTION

In case of the evapopsychrometer the evaporimeter is also the water reservoir for supplying water to the psychrometer, keeping the bulb of one of the thermometers wet by means of a wick which covers the bulb, and is in contact with either a thin layer of water or with an absorptive layer of paper on the bottom of the feeder. The lower end of the vertical water reservoir is not in touch with the bottom of the feeder or with the layer of paper on the bottom of the feeder when in operation; so that water is conducted from the reservoir to the wick and to the bulb of one of the thermometers by capillary action in phase with the rate of evaporation from the wet bulb.

To prevent the water from rushing out of the reservoir it is plugged at its upper end. Consequently, water also seeps in and out of the reservoir from and to the feeder according to the temperature variation of the environment. This variation, however, is averaged out more or less within one day, so that the variation of the height of the water column in the scaled reservoir is related to the evaporated amount of water from the well-defined surface of the thermometer's wetted bulb, since it sits and seals the hole made for the wick on the top of the feeder. Therefore, the evapopsychrometer makes it possible to establish a direct relationship between the recorded rate of evaporation and its own psychrometric data.

The evapopsychrometer can be refilled when needed by establishing a tight contact between the lower end of the reservoir and the bottom of the feeder; thus closing the reservoir from below. Then the plug at the upper end of the reservoir can be removed and it can be refilled. The reversal of this operation makes the evapopsychrometer work again.

DESCRIPTION OF THE INVENTION

Figure 1:
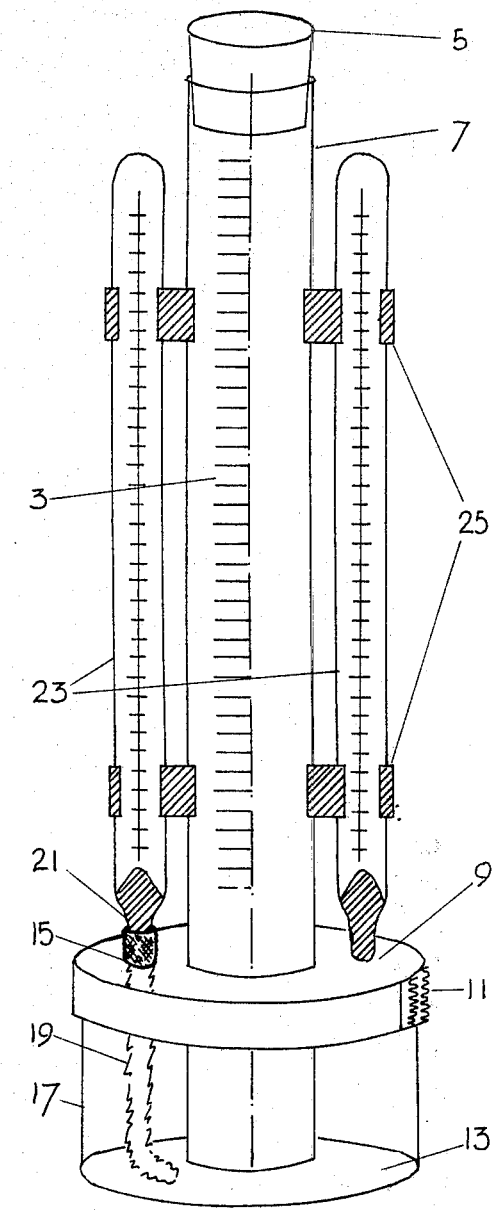
FIG. 1 shows the whole invention.

FIG. 1 depicts the evapopsychrometer in its entirety by the numeral 1. Its main parts are the reservoir 7, the feeder 17, and two thermometers 23. The feeder 17 forms the base of the evapopsychrometer 1. The reservoir 7 which carries a scale 3 to make it possible to record the height of the water level in it, is rigidly fixed to the top 9 of the feeder 17, and penetrates it just a bit further than the depth of the feeder 17. The top 9 is attached to the feeder 17 by screw threads 11 going around outside of the upper rim of the feeder 17 as well as inside the rim of the top 9 or vice versa. On the bottom of the feeder 17 there is a layer of absorptive paper 13. This absorptive paper 13 serves two purposes. On the one hand, it seals the reservoir 7 from below when the top 9 is tightly screwed on the feeder 17. On the other hand, when the top 9 is loose on the feeder 17 and the reservoir 7 contains water, then the absorptive paper 13 conducts water from the reservoir 7 to the wick 19, which covers the bulb 21 of one of the thermometers 23. It is obvious for those versed in the art, however, that the absorptive paper pad 13 could be omitted from the bottom of the feeder 17 without affecting the operation of the evapopsychrometer 1. The wick 19 is led through a hole 15, provided for this purpose on the top 9 of the feeder 17. The upper end of the reservoir 7 is closed by a plug 5.

Figure 3:
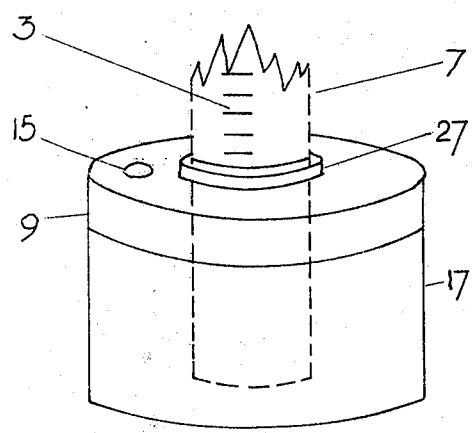
FIG. 3 shows a variation of the lid and reservoir.

FIG. 3 depicts another version of connecting the reservoir 7 and the feeder 17. The alternative solution is provided by a short tube or ring 27 fixed to the lid 9 of the feeder 17 so that the tube of the reservoir 7 can be moved in the ring 27; otherwise ring 27 holds the reservoir 7 in place.

Figure 2:
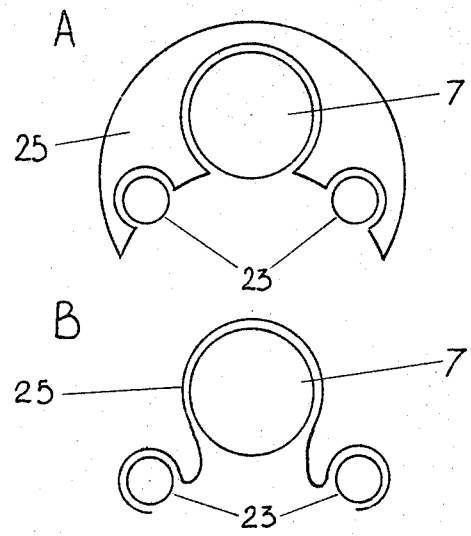
FIG. 2A shows a plan view of one embodiment.
FIG. 2B like FIG. 2A shows a plan view of another embodiment.

The two thermometers 23 are attached to the reservoir 7 by means of clamps 25 which leave all three scales unobstructed (FIG. 2.) It also shows two alternatives to clamp 25. A form of clamp 25 can be made of wire or strip as shown on FIG. 2B. Clamps can also be made from plate material, shown on FIG. 2A. Other similar devices which are known in the art could also be used to hold the thermometers 23 essentially parallel to the reservoir 7.

What is claimed is:

1. An evapopsychrometer having the combination of an evaporimeter with a psychrometer, each of which shares at least one element of the other, for simultaneous measurement of wet and dry bulb temperature and rate of evaporation, said combination comprising;

a thermometer of said psychrometer having a bulb covered by one end of a wick;

a feeder for containing water in closed space into which an opposite end of said wick is extensible; said feeder having a lid means to enclose the top of the feeder and having a hole presenting a rim in the lid means;

said bulb covered by said one end of said wick seated sealingly on said rim to limit the portion of the wick exposed to ambient atmosphere;

said portion of said wick useable to evaporate said water supplied from said feeder;

said evaporimeter having a reservoir means calibrated to measure water evaporated from said portion of said wick;

whereby said evaporimeter shares said portion of said wick with said psychorometer to establish evaporation from the same exact surface area for both the evaporimeter and psychrometer, whereby said portion is said at least one element.

2. An evapopsychrometer as described in claim 1 wherein;

said reservoir means serves to supply all the water to the feeder used in the functioning of the psychrometer, whereby the reservoir means is another shared element.

3. An evapopsychrometer as described in claims 1 or 2 where said lid means is penetrated by said reservoir means with said lid means and said feeder being threadably connected, whereby said reservoir means can be adjusted relative to the bottom of said feeder by turning said lid means.

4. An evapopeychrometer as described in claims 1 or 2 where said reservoir means penetrates said lid means through a short tube or ring fixed to said lid means whereby the lower end of said said reservoir means can be adjusted relative to the bottom of said feeder by sliding it in said ring or said short tube.

* * * * *